(12) United States Patent
Patel et al.

(10) Patent No.: US 8,435,500 B2
(45) Date of Patent: May 7, 2013

(54) NAIL WHITENING COMPOSITION

(75) Inventors: Nishith Patel, Roselle Park, NJ (US); Robert Weber, Suffern, NY (US)

(73) Assignee: L'oréal (FR)

( * ) Notice: Subject to any disclaimer, the term of this patent is extended or adjusted under 35 U.S.C. 154(b) by 1747 days.

(21) Appl. No.: 11/264,458

(22) Filed: Nov. 1, 2005

(65) Prior Publication Data

US 2007/0098654 A1    May 3, 2007

(51) Int. Cl.
*A61K 8/00* (2006.01)
*A61K 8/18* (2006.01)

(52) U.S. Cl.
USPC ............................................ 424/61; 424/400

(58) Field of Classification Search .................. None
See application file for complete search history.

(56) References Cited

U.S. PATENT DOCUMENTS

| | | |
|---|---|---|
| 2,542,897 A | 2/1951 | Brown et al. |
| 5,130,125 A | 7/1992 | Martin et al. |
| 5,888,483 A | 3/1999 | Pahlck et al. |
| 5,935,557 A | 8/1999 | Pahlck et al. |
| 6,051,242 A * | 4/2000 | Patel et al. .................... 424/401 |
| 6,117,118 A | 9/2000 | Laughlin et al. |
| 6,325,783 B1 | 12/2001 | Laughlin et al. |
| 7,048,911 B2 * | 5/2006 | Cashman et al. ............... 424/49 |
| 2003/0152528 A1 * | 8/2003 | Singh et al. .................... 424/53 |
| 2005/0175552 A1 * | 8/2005 | Hoic et al. ...................... 424/49 |
| 2009/0246165 A1 * | 10/2009 | Toreki et al. ............... 424/78.07 |

FOREIGN PATENT DOCUMENTS

| | | |
|---|---|---|
| EP | 0 895 777 A2 | 2/1999 |
| WO | 98/34585 | 8/1998 |

OTHER PUBLICATIONS

"Eureco® HC: A New Active Ingredient for Cosmetic Formulations," Ausimont S.p.A., Viale Lombardia, 20 (2001) Bollate (MI), Italy.

* cited by examiner

*Primary Examiner* — Anand Desai
*Assistant Examiner* — Melissa Mercier
(74) *Attorney, Agent, or Firm* — Lerner, David, Littenberg, Krumholz & Mentlik, LLP

(57) ABSTRACT

A cosmetic composition for bleaching discolored nails containing at least one hydrogen peroxide generator in an amount sufficient to perform bleaching of discolored nails, at least one film forming polymer and at least one cosmetically acceptable volatile solvent. Also disclosed is a method of bleaching discolored nails involving applying onto said nails the cosmetic composition of the present invention.

18 Claims, No Drawings

NAIL WHITENING COMPOSITION

The present invention relates generally to a composition for bleaching discolored fingernails. More particularly, this invention relates to a cosmetic nail composition containing at least one hydrogen peroxide generator that can be applied to discolored fingernails to remove discolorations.

BACKGROUND OF THE INVENTION

The cosmetic appearance of fingernails has long been a matter of concern to consumers. Nails (hereinafter finger nails and toe nails) can become discolored through the use of adhesives for attaching artificial nails or the extensive use of deep red nail polish. In addition, coffee, cigarettes, certain medications, hair coloring products, fruit or vegetable pigments, and the use of harsh chemicals in the home, may also leave the nail undesirably discolored, such as yellow and uneven in color.

Products are available on the market that coat the nail with a nail polish of a slight violet tinge to counteract the discoloration of the nail. However, just like nail polish, these products have limited durability, require frequent reapplication, and function only to mask the nail problem, not to correct it.

In addition, home bleaching remedies are also known. These remedies use oxidizing agents, such as hydrogen peroxide. However, a solution of hydrogen peroxide is usually unstable, requiring lowering its pH. Furthermore, these compositions do not disperse effectively on the nail, thereby lacking an adequate contact between the hydrogen peroxide composition and the stained nail.

Additional products are available for application to nails. One such product is sold under the name Nail SOS® Bleach. It is a water based composition containing sodium hypochlorite, a component of household bleach, potassium hydroxide, Carbomer and a fragrance. While it is thickened, it tends to drip and is slow to dry. Furthermore, it has a strong, unpleasant odor.

U.S. Pat. Nos. 5,888,483 and 5,935,557 provide compositions comprising about 0.01 weight percent to about 10.0 weight percent stabilized hydrogen peroxide, a pH adjusting agent in an amount sufficient to maintain the cosmetic composition at a pH of from about 6 to about 9, a buffer, and water. As these compositions contain a majority of water, they also lack adequate contact with the nail necessitating repeated applications.

An additional problem with these compositions is that the composition is on the surface of the nail and might be transferred through simple contact to articles of clothing, thereby potentially causing staining of the clothes.

Accordingly, a need exists for nail bleaching product that effectively bleaches and removes nail discolorations in a clean, easy and non-transferable manner.

SUMMARY OF THE INVENTION

The present invention is directed to a substantially anhydrous cosmetic composition for bleaching discolored nails containing at least one hydrogen peroxide generator, at least one film former, and at least one cosmetically acceptable volatile solvent.

Another aspect of the present invention is a method of bleaching discolored nails using the above-described cosmetic composition.

DETAILED DESCRIPTION

Other than in the operating examples, or where otherwise indicated, all numbers expressing quantities of ingredients and/or reaction conditions are to be understood as being modified in all instances by the term "about".

The term "substantially anhydrous" means that the composition contains only that amount of water necessary to dissolve the hydrogen peroxide generator present in the final composition, and yet not negatively affect the stability of the final composition. Typically, that amount will be less than 10% by weight, based on the weight of the composition.

The substantially anhydrous nail bleach compositions of the present invention include hydrogen peroxide generator in an amount sufficient to bleach discolored nails, at least one film forming polymer and at least one cosmetically acceptable volatile solvent.

Hydrogen Peroxide Generators

Suitable hydrogen peroxide generators include, but are not limited to, organic peroxides such as carbamide peroxide, peroxide complexes, and inorganic persalts such as the alkali metal perborates, percarbonates, perphosphates, persilicates and persulphates. Preferred inorganic persalts are sodium perborate monohydrate and tetrahydrate, and sodium percarbonate.

Carbamide peroxide is an oxidizing agent also known under the INCI designation of Urea Peroxide. It is an anhydrous addition compound of hydrogen peroxide and urea. It is a powder which is freely soluble in water (about 500 g/l at 20° C.). It is also soluble in glycols. It has the following chemical formula:

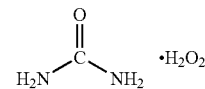

As supplied, it has a minimum hydrogen peroxide concentration of 35% w/w, an active oxygen content of a minimum of 16.5% w/w, and a bulk density of about 650 g/l. A 1% w/w solution in water has a pH value of about 4.0 to 5.2; a 10% w/w solution has a pH value of about 3.0 to 4.2. It may be stabilized with less than 1% w/w sodium pyrophosphate. Its use is known in cosmetic dentistry for whitening teeth, and in the hair industry as a hair bleaching agent. It is available in the form of crystals from Degussa, Parsippany N.J. Its CAS No. is 124-43-6.

Peroxide complexes are stable, solid complexes. They may include, but are not limited to, hydrogen peroxide-polyvinylpyrrolidone (PVP) complexes. These complexes are hydrogen bonded complexes of vinyl pyrrolidone-based polymers with hydrogen peroxide. Molecularly, hydrogen peroxide complexes with vinyl pyrrolidone as a mixture of 1:1 and 1:2 molecular ratios as pictured in the figure below:

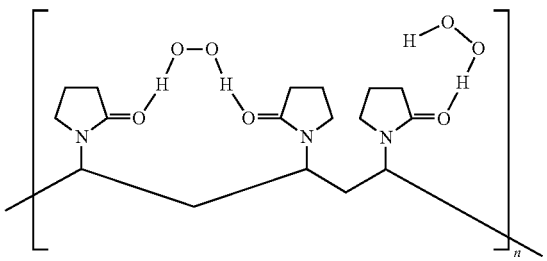

The average of these complexes results in about 20% hydrogen peroxide by weight relative to the amount of vinyl pyrrolidone monomer in the polymer. They are commercially available as Peroxydone® K-30, Peroxydone® K-90 and Peroxydone® KL-10 from ISP, Wayne, N.J. These complexes release hydrogen peroxide upon contact with water.

An example of persalt may include, but is not limited to, sodium perborate which is a true inorganic peroxide containing a cyclic peroxide ring structure. Sodium perborate is produced commercially in both a tetrahydrate and monohydrate form.

The hydrogen peroxide generator present in the nail bleaching composition will slowly release hydrogen peroxide upon contact with water found on the surface of the nails. The hydrogen peroxide will itself decompose and release oxygen thus bleaching the nail discolorations.

The hydrogen peroxide generator can be present in the composition according to the invention in an amount of from 0.1 to 15% by weight, preferably from 1 to 8% by weight, and more preferably from 2 to 5% by weight, all weights being based on the total weight of the composition.

Film-forming Polymer

The composition according to the invention also comprises at least one film-forming polymer. In the present application, the expression "film-forming polymer" means a polymer which is capable, by itself or in the presence of a film-forming auxiliary, of forming an isolable film. The at least one film-forming polymer in the composition can be dissolved or dispersed in the form of particles in the composition according to the invention. The at least one film-forming polymer can be insoluble in water at 25° C., i.e., it is soluble at less than 1% by weight in water at 25° C. (solubility of less than 1% by weight). The at least one film-forming polymer can also, for example, be soluble at 25° C. in at least one organic solvent, such as ethyl acetate and methyl acetate, i.e., it is soluble at greater than 90% by weight in at least one organic solvent at 25° C. (solubility greater than 90% by weight at 25° C.).

Representative film-forming polymers that can be used in the composition of the present invention include, but are not limited to, synthetic polymers, radical-mediated types, polycondensate types, and polymers of natural origin.

The expression "radical-mediated film-forming polymer" means a polymer obtained by polymerization of one or more monomers containing unsaturation, in particular ethylenic unsaturation, certain monomers being capable of homopolymerizing (unlike polycondensates).

The at least one film-forming polymer of radical-mediated type can be chosen from vinyl polymers, and vinyl copolymers, in particular acrylic polymers.

The vinyl film-forming polymers can result from the polymerization of monomers containing ethylenic unsaturation having at least one acid group and/or esters of these acidic monomers and/or amides of these acidic monomers.

Representative monomers bearing an acid group which can be used include α, β-ethylenic unsaturated carboxylic acids, such as acrylic acid, methacrylic acid, crotonic acid, maleic acid and itaconic acid, and, in particular, (meth)acrylic acid and crotonic acid. Among these representative monomers, (meth)acrylic acid can be used.

Representative esters of acid monomers include (meth) acrylic acid esters, also known as (meth)acrylates, especially alkyl(meth)acrylates, in particular of a $C_1$-$C_{20}$ alkyl, such as $C_1$-$C_8$ alkyl; aryl(meth)acrylates, in particular of a $C_6$-$C_{10}$ aryl; and hydroxyalkyl(meth)acrylates, in particular of a $C_2$-$C_6$ hydroxyalkyl.

Representative alkyl(meth)acrylates include methyl methacrylate, ethyl methacrylate, butyl methacrylate, isobutyl methacrylate, 2-ethylhexyl methacrylate and lauryl methacrylate.

Representative hydroxyalkyl(meth)acrylates include hydroxyethyl acrylate, 2-hydroxypropyl acrylate, hydroxyethyl methacrylate and 2-hydroxypropyl methacrylate.

Representative aryl(meth)acrylates include benzyl acrylate and phenyl acrylate.

Among all these representative examples, the (meth) acrylic acid esters may be the alkyl(meth)acrylates.

According to the present invention, the alkyl group of the esters may be substituted, such as fluorinated or perfluorinated, i.e., some or all of the hydrogen atoms in the alkyl group are substituted with fluorine atoms.

Representative amides of the acid monomers include (meth)acrylamides, and especially N-alkyl(meth)acrylamides, in particular of a $C_2$-$C_{12}$ alkyl. Representative N-alkyl (meth)acrylamides include N-ethylacrylamide, N-t-butylacrylamide and N-t-octylacrylamide.

The vinyl film-forming polymers can also result from the homopolymerization or copolymerization of at least one monomer chosen from vinyl esters and styrene monomers. In particular, these monomers can be polymerized with acid monomers and/or esters thereof and/or amides thereof, such as those mentioned above.

Representative vinyl esters include vinyl acetate, vinyl neodecanoate, vinyl pivalate, vinyl benzoate and vinyl t-butylbenzoate.

Styrene monomers which may be mentioned are styrene and α-methylstyrene.

The list of monomers given is not limiting and it is possible to use any monomer known to those skilled in the art which falls within the categories of acrylic and vinyl monomers (including monomers modified with a silicone chain).

Representative acrylic film-forming polymers in aqueous dispersion which can be used according to the invention include those sold by the company Zeneca under the names Neocryl XK-90™, Neocryl A-1070™, Neocryl A-1090™, Neocryl BT-62™, Neocryl A-1079™ and Neocryl A-523™, and those sold by the company Dow Chemical under the name Dow Latex 432™.

Polycondensates which can be used as the at least one film-forming polymer can be anionic, cationic, nonionic or amphoteric and are chosen from polyurethanes, polyurethane-acrylics, polyurethane-polyvinylpyrrolidones, polyester-polyurethanes, polyether-polyurethanes, polyureas and polyurea-polyurethanes.

Representative film-forming polyurethanes can be, for example, aliphatic, cycloaliphatic or aromatic polyurethanes, polyurea-urethanes or polyurea copolymers, comprising:

(i) at least one sequence originating from monomers chosen from aliphatic monomers, cycloaliphatic monomers, aromatic polyester monomers, branched and non-branched silicone monomers, such as polydimethylsiloxane and polymethylphenylsiloxane, and monomers comprising fluoro groups.

(ii) Representative film-forming polyurethane polymers in aqueous dispersion, according to the invention, include polyester-polyurethanes sold under the names "Avalure UR-405™", "Avalure UR-410™", "Avalure $UR_{425}$™", "Avalure UR-450™" and "Sancure 2060™" by the company Goodrich and the polyether-polyurethanes sold under the names "Sancure 878™" by the company Goodrich and "Neorez R 970™" by the company Zeneca.

Representative film-forming polycondensates include polyesters, polyesteramides, fatty-chain polyesters, polyamides and epoxyester resins, resins resulting from the condensation of formaldehyde with an arylsulphonamide, and arylsulphonamide epoxy resins.

The polyesters can be obtained, in a known manner, by polycondensation of dicarboxylic acids with polyols, in particular diols.

The dicarboxylic acid can be aliphatic, alicyclic or aromatic. Representative acids include oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalene-dicarboxylic acid and 2,6-naphthalene-dicarboxylic acid. These dicarboxylic acid monomers can be used alone or in combinations of at least two dicarboxylic acid monomers. Phthalic acid, isophthalic acid, and terephthalic acid can be chosen from among the representative acids.

Representative diols can be chosen from aliphatic, alicyclic, and aromatic diols, such as ethylene glycol, diethylene glycol, triethylene glycol, 1,3-propanediol, cyclohexanedimethanol, and 4-butanediol. Other representative polyols include glycerol, pentaerythritol, sorbitol, and trimethylolpropane.

The polyesteramides can be obtained in a similar manner to the polyesters by polycondensation of diacids with diamines or with amino alcohols. Representative diamines include ethylenediamine, hexamethylenediamine, and meta- and para-phenylene-diamine. A representative amino alcohol is monoethanolamine.

The polyester can also comprise at least one monomer bearing at least one group —$SO_3M$, with M representing a hydrogen atom, an ammonium ion $NH^+$ or a metal ion such as, for example, an $Na^+$, $Li^+$, $K^+$, $Mg^{2+}$, $Ca^{2+}$, $Cu^{2+}$, $Fe^{2+}$, or $Fe^{3+}$ ion. A difunctional aromatic monomer comprising such a group —$SO_3M$ is representative.

The aromatic nucleus of the difunctional aromatic monomer also bearing a group —$SO_3M$ as described above can be chosen, for example, from benzene, naphthalene, anthracene, diphenyl, oxydiphenyl, sulphonyldiphenyl, and methylenediphenyl nuclei. Examples of difunctional aromatic monomers also bearing a group —$SO_3M$ include sulpho-isophthalic acid, sulphoterephthalic acid, sulphophthalic acid, and 4-sulphonaphthalene-2,7-dicarboxylic acid.

Copolymers based on isophthalate/sulphoisophthalate, and more particularly copolymers obtained by condensation of diethylene glycol, cyclohexanedimethanol, isophthalic acid, and sulphoisophthalic acid, can be used in the compositions forming the subject of the invention. Such polymers are sold, for example, under the brand name Eastman AQ by the company Eastman Chemical Products.

Representative optionally modified polymers of natural origin include shellac resins, sandaraque gums, dammar resins, elemis gums, copal resins, and cellulose-derived polymers, such as nitrocellulose, cellulose acetate, cellulose acetobutyrate, cellulose acetopropionate, and ethylcellulose.

The at least one film-forming polymer may be present in the composition according to the invention in an amount of from 0.1 to 40% by weight, preferably from 1 to 30% by weight, and more preferably from 2 to 20% by weight, all weights based on the weight of the total composition.

Cosmetically Acceptable Volatile Solvent

According to the invention, the composition also comprises at least one cosmetically acceptable volatile solvent. Examples of suitable solvents include, but are not limited to:

a) ketones that are liquid at room temperature, such as methyl ethyl ketone, methyl isobutyl ketone, diisobutyl ketone, isophorone, cyclohexanone, and acetone;

b) alcohols that are liquid at room temperature, such as ethanol, isopropanol, diacetone alcohol, 2-butoxyethanol, and cyclohexanol;

c) glycols that are liquid at room temperature, such as ethylene glycol, propylene glycol, pentylene glycol, and glycerol;

d) propylene glycol ethers that are liquid at room temperature, such as propylene glycol monomethyl ether, propylene glycol monomethyl ether acetate, and dipropylene glycol mono-n-butyl ether;

e) short-chain esters, containing from 3 to 8 carbon atoms in total, such as ethyl acetate, methyl acetate, propyl acetate, n-butyl acetate, and isopentyl acetate;

f) ethers that are liquid at room temperature, such as diethyl ether, dimethyl ether, or dichlorodiethyl ether;

g) alkanes that are liquid at room temperature, such as decane, heptane, dodecane, and cyclohexane;

h) cyclic aromatic compounds that are liquid at room temperature, such as toluene and xylene;

i) aldehydes that are liquid at room temperature, such as benzaldehyde and acetaldehyde.

The at least one cosmetically acceptable volatile solvent may be present in an amount ranging from 30 to 99% by weight, preferably from 50 to 90% by weight, and more preferably from 60 to 80% by weight, all weights being based on the total weight of the composition.

To improve the film-forming properties of the composition according to the invention, at least one film-forming auxiliary agent may be provided.

When the at least one film-forming auxiliary agent is used with the at least one film-forming polymer, the at least one film-forming auxiliary agent can be chosen from any compound known to those skilled in the art as being capable of fulfilling the desired function, and can be chosen in particular from plasticizers.

The nail bleaching composition disclosed herein may comprise at least one film-forming aid for improving the film-forming properties of the varnish.

The at least one film-forming aid may be chosen from any compounds known by persons skilled in the art to be capable of fulfilling the desired function, such as those chosen from plasticizing agents.

The plasticizing agents include, but are not limited to:

a) citrates such as triethyl citrate, tributyl citrate, triethyl acetylcitrate, tributyl acetylcitrate, and 2-triethylhexyl acetylcitrate;

b) phthalates such as diethyl phthalate, dibutyl phthalate, dioctyl phthalate, dipentyl phthalate, and dimethoxyethyl phthalate;

c) tricresyl phosphate, benzyl benzoate, tributyl phosphate, butyl acetylricinoleate, glyceryl acetylricinoleate, butyl glycolate, tributoxyethyl phosphate, triphenyl phosphate, dibutyl tartrate, camphor, glyceryl triacetate, N-ethyl-o,p-toluenesulphonamide, and mixtures thereof.

The at least one film-forming aid, such as the plasticizing agent, may be present in an amount, by weight, relative to the total weight of the composition, generally ranging from 0.1 to 15% by weight, preferably from 1 to 10% by weight, all weights being based on the total weight of the composition.

Additional ingredients, such as vitamins, glycerin, healing agents and treatment agents, fragrances, botanical extracts, colorants, optical brighteners may also be added to the cosmetic composition for bleaching nails.

Panthenol is a preferred vitamin for use in the present invention. It is preferably present at a concentration of from 0.01 to 3% by weight, all weights being based on the total weight of the composition.

Glycerin acts to moisturize the nails and cuticles. Glycerin is preferably present in an amount ranging from 0.1 to 5%, preferably from 0.5 to 3% by weight, all weights being based on the total weight of the composition.

The healing agents may include, for example, green tea extract or aloe or a combination thereof. The treatment agents may include, for example, aldehyde.

A fragrance may be added to the nail bleach composition to enhance its appeal and acceptability. The fragrance is preferably present at up to about 5 weight percent. The fragrance is most preferably present in a range about 0.0001 to about 1.0 weight percent. Any compatible cosmetic fragrance may be used. Compatible means that the fragrance works with the system without any deleterious effects.

Botanical extracts may also be present. One such extract is Lemon Peel Extract.

It is well known in the nail enamel art that water is not well tolerated in the formulation as it may not be compatible/soluble with the at least one organic solvent. The hydrogen peroxide generator may be solubilized in water, or a lower alcohol, or a polyol such as a glycol.

The following is an example of a cosmetic nail bleaching composition.

EXAMPLE

Nail Whitening Composition

| INCI names US | % W/W |
|---|---|
| Urea Peroxide | 2.542 |
| Tributyl Citrate | 2.44 |
| Acetanilid | 0.05083 |
| Citric Acid | 0.02577 |
| Violet 2 | 0.00032 |
| Titanium Dioxide (And) Oxidized Polyethylene | 0.025 |
| Stearalkonium Hectorite | 0.64655 |
| Nitrocellulose (And) Isopropyl Alcohol | 9.88951 |
| Phthalic Anhydride/Glycerin/Glycidyl Decanoate Copolymer | 3.78714 |
| Butyl Acetate (And) Acrylates Copolymer | 2.49 |
| Isopropyl Alcohol | 2.35168 |
| Ethyl Acetate | 31.45098 |
| Water | 2.112585 |
| Acetyl Tributyl Citrate | 0.01579 |
| Glycerin | 1.49 |
| Butyl Acetate | 39.559845 |
| Lemon Peel Extract | 1.122 |
| TOTAL | 100 |

The nail whitening formulation of the above example was used daily for a period of two weeks and changes in color were determined. Measurements were taken with the Minolta CR 300 Chromameter using the Yellowness Index (YI). The Yellowness index method (ASTM YI E313 method or Yellowness Index: Standard Method for Indexes of Whiteness and Yellowness of Near-White, Opaque and Plastics) was used to measure the change in yellowing of the nail. A decrease in the Y value over time would indicate that less yellowing was detected over time. The results are reported for the thumb only as its surface is the most reliable for providing accurate data.

TABLE 1

Raw results of measure of Yellowness Index per ASTM Method ASTM YI E313 with ten panelists.

| | | Panelist 1 YI | Panelist 2 YI | Panelist 3 YI | Panelist 4 YI | Panelist 5 YI |
|---|---|---|---|---|---|---|
| 1 | Thumb @ Day 1 | 31.6079 | 52.7269 | 54.2566 | 36.189 | 37.9309 |
| 2 | Thumb @ Day 7 | 35.7375 | 48.4581 | 48.9937 | 31.8462 | 40.7584 |
| 3 | Thumb @ Day 14 | | 43.694 | 49.9092 | 32.4635 | 33.9769 |
| | Difference After 1 Week | 4.1296 | −4.2688 | −5.2629 | −4.3428 | 2.8275 |
| | Difference After 2 Weeks | N/A | −9.0329 | −4.3474 | −3.7255 | −3.954 |

| | | Panelist 6 YI | Panelist 7 YI | Panelist 8 YI | Panelist 9 YI | Panelist 10 YI |
|---|---|---|---|---|---|---|
| 1 | Thumb @ Day 1 | 37.2552 | 33.9531 | 37.5192 | 33.9531 | 35.5674 |
| 2 | Thumb @ Day 7 | 35.2876 | 33.5813 | 35.6402 | 33.5813 | 34.8437 |
| 3 | Thumb @ Day 14 | 34.1693 | 31.2256 | 35.6913 | 31.2256 | 33.5417 |
| | Difference After 1 Week | −1.9676 | −0.3718 | −1.879 | −0.3718 | −0.7237 |
| | Difference After 2 Weeks | −3.0859 | −2.7275 | −1.8279 | −2.7275 | −2.0257 |

TABLE 2

Mean (± Standard Deviation) of yellowness measurements on thumbs [N = 9]

| | Day 1 | Day 7 | Day 14 | p-Value |
|---|---|---|---|---|
| YI | 39.93 (±7.83) | 38.11 (±6.50) | 36.21 (±6.36) | 0.001 (Day 1 > Day 14) |

The YI values for day 14 were statistically significantly smaller than those of day 1 (P=0.001), showing a statistically significant decrease in the Yellowness Index due to the use of the nail bleaching composition of the present invention.

The present invention having been thus described with particular reference to the preferred forms thereof, it will be obvious that various changes and modifications may be made therein without departing from the spirit and scope of the invention as defined in the appended claims.

What is claimed is:

1. A cosmetic composition for bleaching discolored nails comprising:
   a) at least one hydrogen peroxide generator in an amount sufficient to bleach said nails, wherein the hydroxide generator is selected from the group consisting of carbamide peroxide, sodium percarbonate, sodium perborate monohydrate, and sodium perborate tetrahydrate;
   b) at least one film forming polymer selected from the group consisting of (i) a polyurethane polymer selected from the group consisting of polyurethane-acrylics, polyurethane-polyvinylpyrrolidones, polyester-polyurethanes, polyether-polyurethanes, and polyurea-polyurethanes; (ii) polyurea; (iii) polyurea copolymers; (iv) polyesters produced by condensation of a dicarboxylic acid and a diol; (v) polyesteramides; (vi) fatty-chain polyesters; (vii) copolymers based on isophthalate/sulphoisophthalate; and (viii) arylsulfonamide epoxy resins, and
   c) at least one cosmetically acceptable volatile solvent, wherein the composition is anhydrous or substantially anhydrous and contains water in an amount less than 10% by weight of the composition, and wherein the composition does not contain a colorant.

2. A cosmetic composition according to claim 1 wherein the at least one hydrogen peroxide generator is chosen from the group consisting of sodium perborate monohydrate, sodium perborate tetrahydrate and sodium percarbonate.

3. A cosmetic composition according to claim 1 wherein the at least one hydrogen peroxide generator is carbamide peroxide.

4. A cosmetic composition according to claim 1 wherein the at least one hydrogen peroxide generator is present in an amount of from about 0.1 to about 15% by weight, based on the total weight of the composition.

5. A cosmetic composition according to claim 1 wherein the at least one hydrogen peroxide generator is present in an amount of from about 2 to about 5% by weight, all weights being based on the total weight of the composition.

6. A cosmetic composition according to claim 1 wherein the at least one film former is present in an amount of from about 0.1 to about 40% by weight, all weights being based on the total weight of the composition.

7. A cosmetic composition according to claim 1 wherein the at least one film former is present in an amount of from about 2 to about 20% by weight, all weights being based on the total weight of the composition.

8. A cosmetic composition according to claim 1 wherein the at least one cosmetically acceptable volatile solvent is present in an amount of from about 30 to about 99% by weight, all weights being based on the total weight of the composition.

9. A cosmetic composition according to claim 1 wherein the at least one cosmetically acceptable solvent is present in an amount of from about 60 to about 80% by weight, all weights being based on the total weight of the composition.

10. A method of bleaching discolored nails comprising applying onto said discolored nails a composition containing:
   a) at least one hydrogen peroxide generator in an amount sufficient to bleach said nails, wherein the hydroxide generator is selected from the group consisting of carbamide peroxide, sodium percarbonate, sodium perborate monohydrate, and sodium perborate tetrahydrate;
   b) at least one film forming polymer selected from the group consisting of (i) a polyurethane polymer selected from the group consisting of polyurethane-acrylics, polyurethane-polyvinylpyrrolidones, polyester-polyurethanes, polyether-polyurethanes, and polyurea-polyurethanes; (ii) polyurea; (iii) polyurea copolymers; (iv) polyesters produced by condensation of a dicarboxylic acid and a diol; (v) polyesteramides; (vi) fatty-chain polyesters; (vii) copolymers based on isophthalate/sulphoisophthalate; and (viii) arylsulfonamide epoxy resins, and
   c) at least one cosmetically acceptable volatile solvent, wherein the composition is anhydrous or substantially anhydrous and contains water in an amount less than 10% by weight of the composition, and wherein the composition does not contain a colorant.

11. A method of bleaching discolored nails according to claim 10 wherein the at least one hydrogen peroxide generator is chosen from the group consisting of sodium perborate monohydrate, sodium perborate tetrahydrate and sodium per carbonate.

12. A method of bleaching discolored nails according to claim 10 wherein the at least one hydrogen peroxide generator is carbamide peroxide.

13. A method of bleaching discolored nails according to claim 10 wherein the at least one hydrogen peroxide generator is present in an amount of from about 0.1% to about 15% by weight, all weights being based on the total weight of the composition.

14. A method of bleaching discolored nails according to claim 10 wherein the at least one hydrogen peroxide generator is present in an amount of from about 2 to about 5% by weight, all weights being based on the total weight of the composition.

15. A method of bleaching discolored nails according to claim 10 wherein the at least one film former is present in an amount of from about 0.1 to about 40% by weight, all weights being based on the total weight of the composition.

16. A method of bleaching discolored nails according to claim 10 wherein the at least one film former is present in an amount of from about 2 to about 20% by weight, all weights being based on the total weight of the composition.

17. A method of bleaching discolored nails according to claim 10 wherein the at least one cosmetically acceptable volatile solvent is present in an amount of from about 30 to about 99% by weight, all weights being based on the total weight of the composition.

18. A method of bleaching discolored nails according to claim 10 wherein the at least one cosmetically acceptable volatile solvent is present in an amount of from about 60 to about 80% by weight, all weights being based on the total weight of the composition.

* * * * *